United States Patent
Kojima et al.

(10) Patent No.: US 10,492,695 B2
(45) Date of Patent: Dec. 3, 2019

(54) LIVING-BODY INFORMATION MEASURING DEVICE AND LIGHT-EMITTING ELEMENT

(71) Applicant: FUJI XEROX CO., LTD., Tokyo (JP)

(72) Inventors: Tomoaki Kojima, Kanagawa (JP); Kazuhiro Sakai, Kanagawa (JP); Hideaki Ozawa, Kanagawa (JP); Hideyuki Umekawa, Kanagawa (JP); Manabu Akamatsu, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 476 days.

(21) Appl. No.: 15/230,679

(22) Filed: Aug. 8, 2016

(65) Prior Publication Data

US 2017/0273570 A1    Sep. 28, 2017

(30) Foreign Application Priority Data

Mar. 28, 2016    (JP) .................................. 2016-064463

(51) Int. Cl.
    *A61B 5/0205*    (2006.01)
    *A61B 5/026*     (2006.01)
    (Continued)

(52) U.S. Cl.
    CPC .......... *A61B 5/0205* (2013.01); *A61B 5/0261* (2013.01); *A61B 5/14552* (2013.01);
    (Continued)

(58) Field of Classification Search
    CPC ..... A61B 5/0205; A61B 5/145; A61B 5/0261; A61B 5/7225; A61B 5/02416; A61B 2562/0233; A61B 5/7257
    See application file for complete search history.

(56) References Cited

U.S. PATENT DOCUMENTS

| | | | | |
|---|---|---|---|---|
| 5,676,141 A | * | 10/1997 | Hollub | ............... A61B 5/14551 356/41 |
| 6,253,097 B1 | * | 6/2001 | Aronow | ............. A61B 5/14552 600/310 |

(Continued)

FOREIGN PATENT DOCUMENTS

| JP | 2008-212258 A | 9/2008 |
|---|---|---|
| JP | 4475601 B2 | 6/2010 |
| JP | 2013-000158 A | 1/2013 |

OTHER PUBLICATIONS

Communication dated Jul. 22, 2019 from the China National Intellectual Property of Administration in counterpart Application No. 201610803799.7.

*Primary Examiner* — Eric F Winakur
*Assistant Examiner* — Abid A Mustansir
(74) *Attorney, Agent, or Firm* — Sughrue Mion, PLLC (57) ABSTRACT

A living-body information measuring device includes a first light-emitting unit that emits a single-mode laser beam, a second light-emitting unit that emits a multi-mode light beam or an LED light beam, a light-receiving element that receives reflected or transmitted light beams reflected or transmitted by a living body when the first light-emitting unit and the second light-emitting unit emit the beams toward the living body, a control unit that controls light-emission periods of the first light-emitting unit and the second light-emitting unit, and a measurement unit that measures plural types of living-body information about the living body by using each of the reflected or transmitted light beams that are successively received by the light-receiving element.

11 Claims, 7 Drawing Sheets

(51) Int. Cl.
*A61B 5/1455* (2006.01)
*A61B 5/00* (2006.01)
*A61B 5/024* (2006.01)

(52) U.S. Cl.
CPC ........ *A61B 5/7225* (2013.01); *A61B 5/02416* (2013.01); *A61B 5/7257* (2013.01); *A61B 2562/0233* (2013.01)

(56) References Cited

U.S. PATENT DOCUMENTS

| | | | |
|---|---|---|---|
| 2005/0234315 A1* | 10/2005 | Mayevsky | A61B 5/0059 600/310 |
| 2006/0089546 A1* | 4/2006 | Mahony | A61B 5/0064 600/310 |
| 2006/0285570 A1* | 12/2006 | Xuan | H01S 5/1021 372/68 |
| 2013/0338461 A1* | 12/2013 | Lamego | A61B 5/14551 600/324 |
| 2017/0251936 A1* | 9/2017 | Sawado | A61B 8/4227 |

* cited by examiner

LIVING-BODY INFORMATION MEASURING DEVICE AND LIGHT-EMITTING ELEMENT

CROSS-REFERENCE TO RELATED APPLICATIONS

This application is based on and claims priority under 35 USC 119 from Japanese Patent Application No. 2016-064463 filed Mar. 28, 2016.

BACKGROUND (i) Technical Field

The present invention relates to a living-body information measuring device and a light-emitting element.

(ii) Related Art

Examples of a known technology for measuring living-body information include a photoplethysmographic sensor that measures a photoplethysmogram by using absorption of light by hemoglobin, and an oxygen saturation sensor that measures oxygen saturation by using dual-wavelength photoplethysmography. In recent years, blood flow sensors that detect blood flow information by using a Doppler shift of light caused by the velocity of red blood cells have been developed. Using advanced manufacturing technologies, the sizes of such blood flow sensors have been reduced so as to be attachable to a fingertip. The blood flow sensors are capable of measuring blood flow information, such as a blood flow, a blood velocity, and a blood volume.

Until recently, a single sensor device was used to measure a single type of living-body information. Recently, however, wearable devices that are each capable of measuring plural types of living-body information have been actively developed. In order to develop wearable devices that are capable of measuring plural types of living-body information, it is necessary to reduce the size and the cost of a sensor.

When simultaneously measuring the photoplethysmograph (or oxygen saturation) and blood flow information of a living body by irradiating the living body with light, it is necessary to use a single-mode laser beam, which has a narrower light-emission-spectrum width, to measure the blood flow information. However, the light-emission amount of a single-mode laser beam is small. On the other hand, it is necessary to use a light beam having a large light-emission amount to measure the photoplethysmogram (or oxygen saturation). Therefore, if a single-mode laser beam is used, the light-emission amount may be insufficient. Moreover, if a single-mode laser beam is used, the Doppler shift may generate noise.

Summary

According to an aspect of the invention, a living-body information measuring device includes a first light-emitting unit that emits a single-mode laser beam, a second light-emitting unit that emits a multi-mode light beam or an LED light beam, a light-receiving element that receives reflected or transmitted light beams reflected or transmitted by a living body when the first light-emitting unit and the second light-emitting unit emit the beams toward the living body, a control unit that controls light-emission periods of the first light-emitting unit and the second light-emitting unit, and a measurement unit that measures plural types of living-body information about the living body by using each of the reflected or transmitted light beams that are successively received by the light-receiving element.

BRIEF DESCRIPTION OF THE DRAWINGS

An exemplary embodiment of the present invention will be described in detail based on the following figures, wherein.

DETAILED DESCRIPTION

Hereinafter, an exemplary embodiment of the present invention will be described with reference to the drawings. In all of the drawings, elements that perform the same operations or have the same functions will be denoted by the same numerals, and redundant descriptions of such elements will be omitted.

Figure 1:
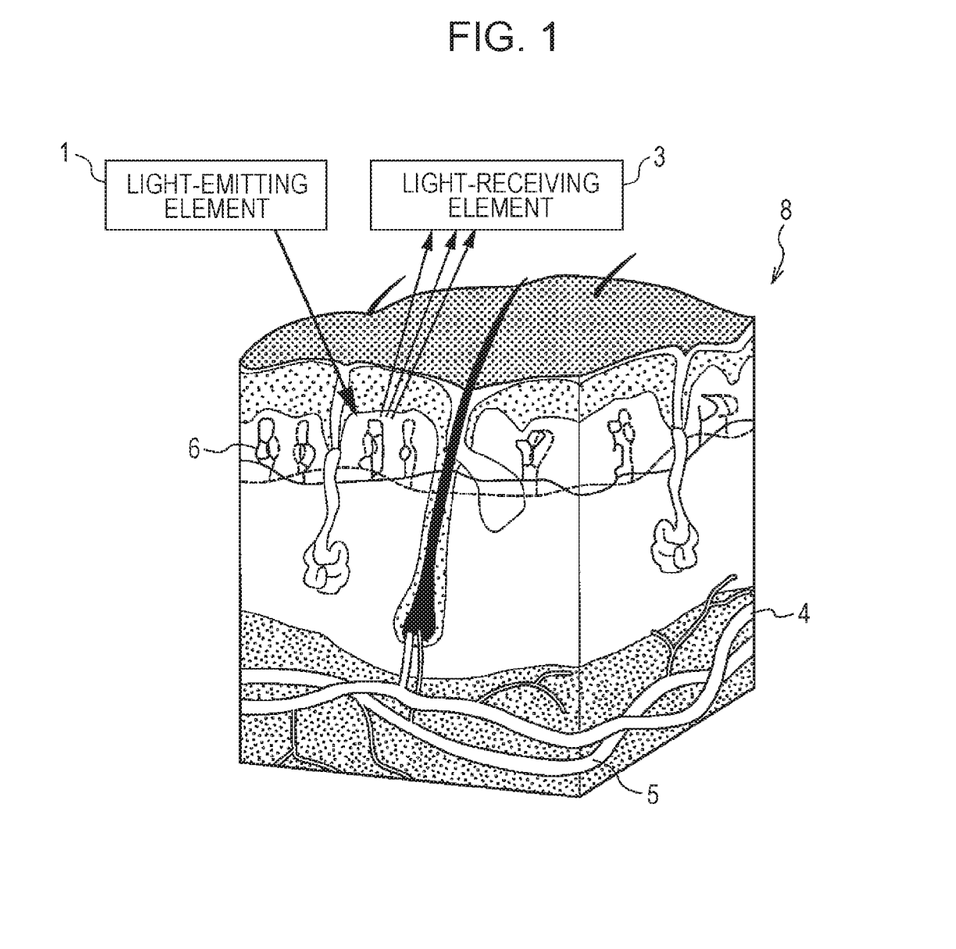
FIG. 1 is a schematic view illustrating an example of measurement of a blood flow information and blood oxygen saturation.

Referring to FIG. 1, a method of measuring blood flow information and blood oxygen saturation, which are examples of living-body information related to blood, will be described.

As illustrated in FIG. 1, blood flow information and blood oxygen saturation are measured by emitting light from a light-emitting element 1 toward a patient's body (living body 8); receiving light that is reflected or transmitted by an artery 4, a vein 5, a capillary vessel 6, or the like in the patient's body by using a light-receiving element 3; and by measuring the intensity of the received light, that is, the amount of reflected or transmitted light received by the light-receiving element 3.

Measurement of Blood Flow Information

Figure 2:
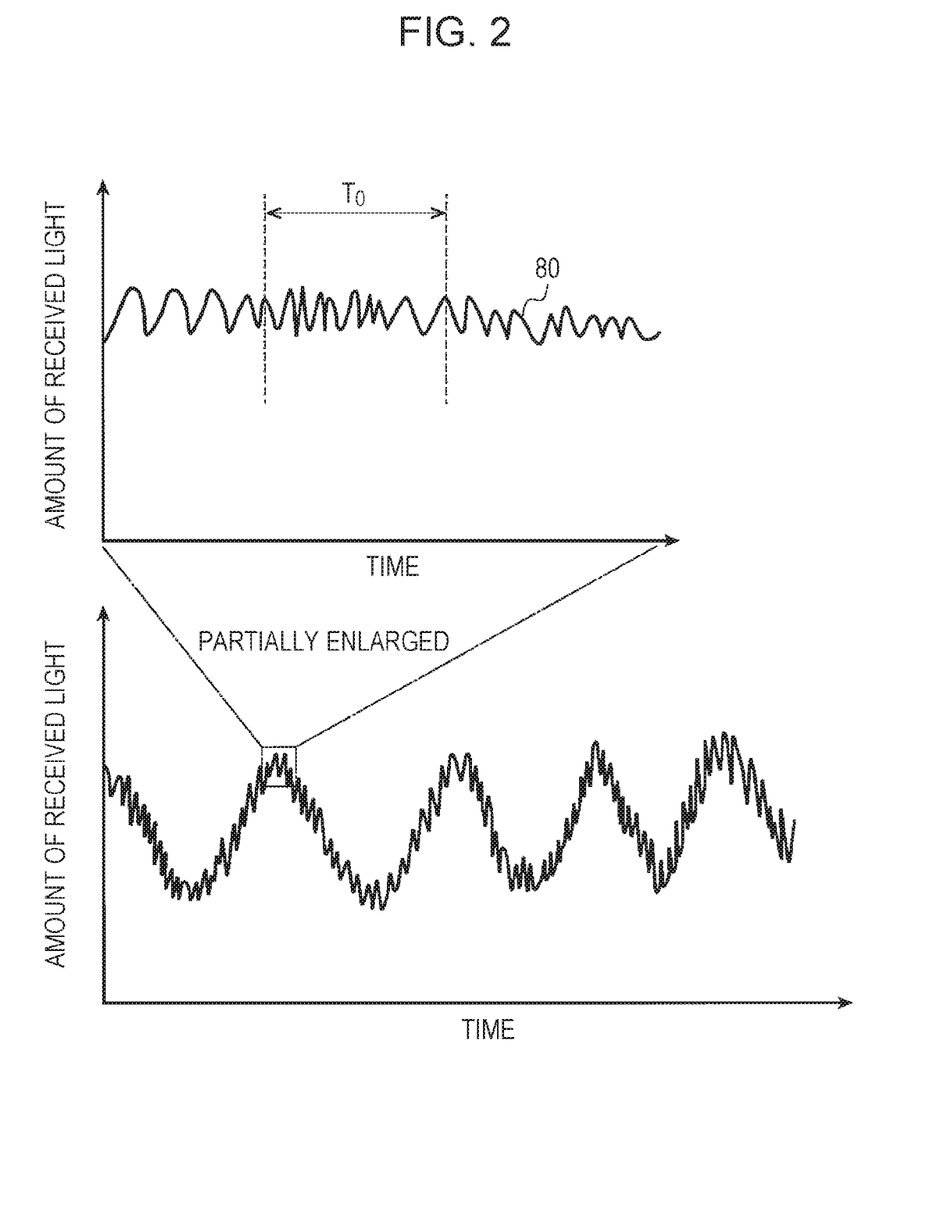
FIG. 2 a graph illustrating one example of a change in an amount of received light due to reflected light from a living body.

FIG. 2 illustrates graphs showing a curve 80 that represents an example the amount of reflected light received by the light-receiving element 3. In the graph of FIG. 2, the horizontal axis represents the time and the vertical axis represents the output of the light-receiving element 3, that is, the amount of light received by the light-receiving element 3.

As illustrated in FIG. 2, the amount of light received by the light-receiving element 3 changes with time. It is considered that this change occurs due to the following three optical phenomena that occur when the living body 8, including blood vessels, is irradiated with light.

The first optical phenomenon is a change in absorption of light that occurs due to a change in the volume of blood existing in a blood vessel that is being measured by pulsation. The blood includes blood cells, such as red blood cells, and the blood moves in a blood vessel, such as the capillary vessel 6. Therefore, when the blood volume changes, the number of blood cells that move in the blood vessel also changes. This change may influence the amount of light received by the light-receiving element 3.

The second optical phenomenon is an influence of a Doppler shift.

Figure 3:
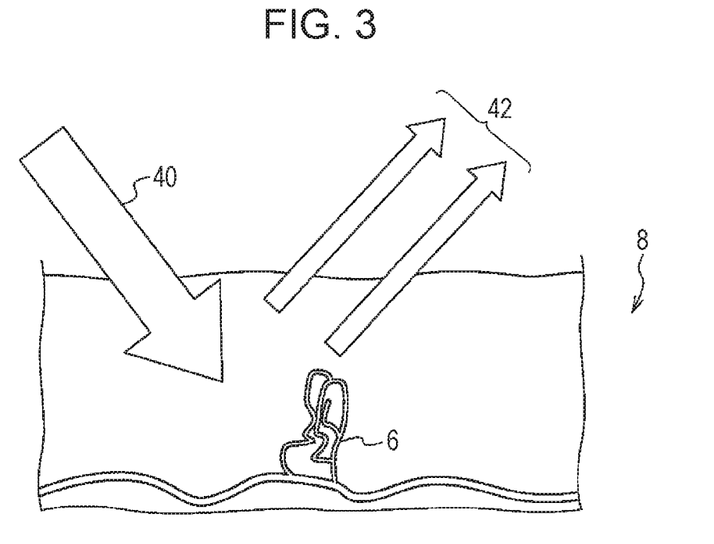
FIG. 3 is a schematic view used to explain a Doppler shift that occurs when a blood vessel is irradiated with a laser beam or a transmissive light beam.

FIG. 3 illustrates a case where, for example, the light-emitting element 1 emits a coherent light beam 40, such as a laser beam, having a frequency $\omega_0$ toward a region including the capillary vessel 6, which is an example of a blood vessel. In this case, a Doppler shift, having a frequency difference $\Delta\omega_0$, occurs in a part of a scattered light 42 that is generated due to scattering of the coherent light beam 40 by blood cells moving in the capillary vessel 6. The frequency difference $\Delta\omega_0$ is determined by the moving speed of the blood cells. In contrast, another part of the scattered light 42 that is generated due to scattering of the coherent light beam 40 by an organ (stationary tissues) that does not include moving components, such as blood cells, has a frequency that is the same as the frequency $\omega_0$ of the emitted light beam. Accordingly, the part of the scattered light 42 having a frequency $(\omega_0+\Delta\omega_0)$, which is scattered by a blood vessel, such as the capillary vessel 6, and the other part of the scattered light 42 having the frequency $\omega_0$, which is scattered by a stationary tissues, interfere with each other. As a result, a beat signal having the frequency difference $\Delta\omega_0$ is observed by the light-receiving element 3, and the amount of light received by the light-receiving element 3 changes with time. The frequency difference $\Delta\omega_0$ of the beat signal observed by the light-receiving element 3, which depends on the moving speed of blood cells, is within a range having an upper limit of several tens of kilohertz.

The third optical phenomenon is an influence of speckles.

Figure 4:
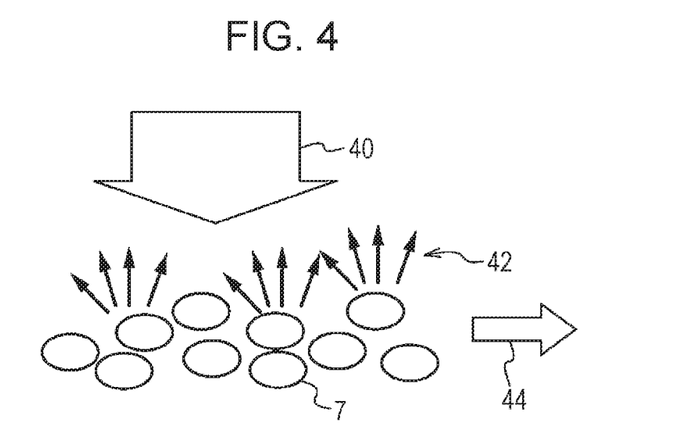
FIG. 4 is a schematic view used to explain speckles that occur when a blood vessel is irradiated with a laser beam.

FIG. 4 illustrates a case where the light-emitting element 1 emits the coherent light beam 40, such as a laser beam, toward blood cells 7, such as red blood cells, that move in the direction of an arrow 44. In this case, the laser beam is scattered by the blood cells 7 in various directions. The scattered light, which have different phases, interfere with each other randomly. Thus, a light intensity distribution having a random spotted pattern occurs. A light intensity distribution pattern formed in this way is referred to as a "speckle pattern".

As described above, because the blood cells 7 move in the blood vessel, the way in which light is scattered by the blood cells 7 changes, and the speckle pattern varies with time. Accordingly, the amount of light received by the light-receiving element 3 changes with time.

Figure 5:
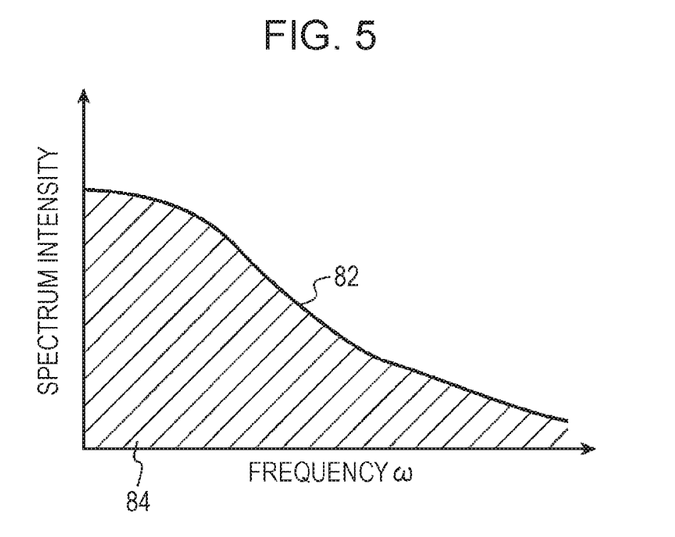
FIG. 5 is a graph illustrating one example of a spectrum distribution with respect to a change in an amount of light received light.

Next, an example of a method of obtaining blood flow information will be described. Referring to FIG. 2, when the time-series data of the amount of light received by the light-receiving element 3 is obtained, a part of the data in a predetermined unit time $T_0$ is cut out. By performing, for example, fast Fourier transform (FFT) on the data, a spectrum distribution for the frequency $\omega$ is obtained. FIG. 5 is a graph showing a curve 82 representing an example of the spectrum distribution for the frequency $\omega$ in the unit time $T_0$. In the graph of FIG. 5, the horizontal axis represents the frequency $\omega$, and the vertical axis represents the spectrum intensity.

The blood volume is proportional to a value obtained by normalizing, with respect to the total light amount, the area of power spectrum, which is represented by a hatched region 84 surrounded by the curve 82, the horizontal axis, and the vertical axis of the graph of FIG. 5. The blood velocity is proportional to the average frequency of the power spectrum represented by the curve 82. Therefore, the blood velocity is proportional to a value obtained by dividing the integral of the product of the frequency $\omega$ and the power spectrum at the frequency $\omega$ with respect to the frequency $\omega$ by the area of the hatched region 84.

The blood flow, which is the product of the blood volume and the blood velocity, is obtained by using the aforementioned formulas for calculating the blood volume and the blood velocity. The blood flow, the blood velocity, and the blood volume are examples of blood flow information. However, blood flow information is not limited to these.

Figure 6:
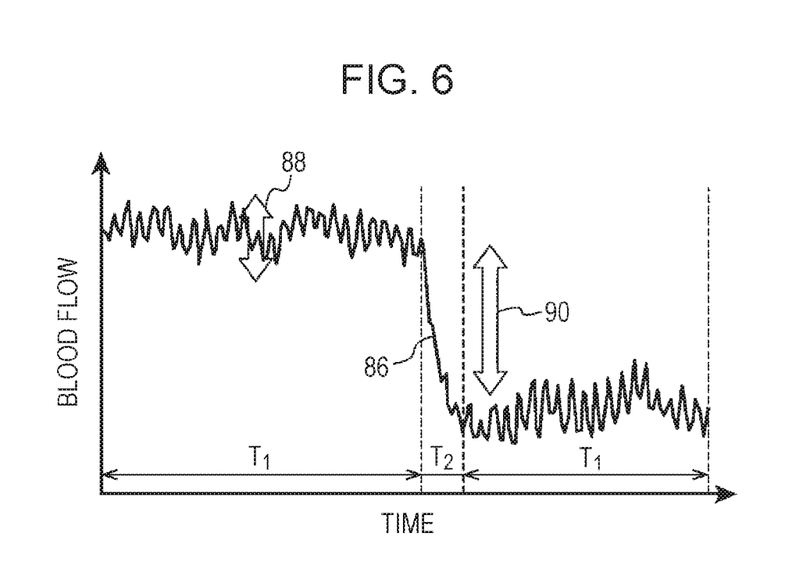
FIG. 6 is a graph illustrating one example of a change in blood flow information.

FIG. 6 is a graph showing a curve 86 representing an example of the calculated change in the blood flow per unit time T0. In the graph of FIG. 6, the horizontal axis represents the time and the vertical axis represents the blood flow.

As illustrated in FIG. 6, the blood flow varies with time, and the trend of the variation is divided into two types. For example, a variation range 90 of the blood flow in an interval $T_2$ of FIG. 6 is larger than a variation range 88 of the blood flow in an interval $T_1$ of FIG. 6. Presumably, this is because the change in the blood flow in the interval $T_1$ is mainly due to pulsation and the change in the blood flow in the interval $T_2$ is due to, for example, congestion.

When measuring the blood flow, in order to measure a Doppler shift, a single-mode laser is used as the light-emitting element 1 for measuring the blood flow. This is because a single-mode laser emits a single-mode laser beam, which has a smaller light-emission-spectrum width than other light beams. Hereinafter, a single-mode laser that is used to measure the blood flow will be referred to as a "light-emitting element LD1".

Measurement of Oxygen Saturation

Next, measurement of blood oxygen saturation will be described. Blood oxygen saturation is an indicator of the degree to which oxygen is bound to hemoglobin in the blood. As the blood oxygen saturation decreases, symptoms such as anemia are increasingly likely to occur.

Figure 7:
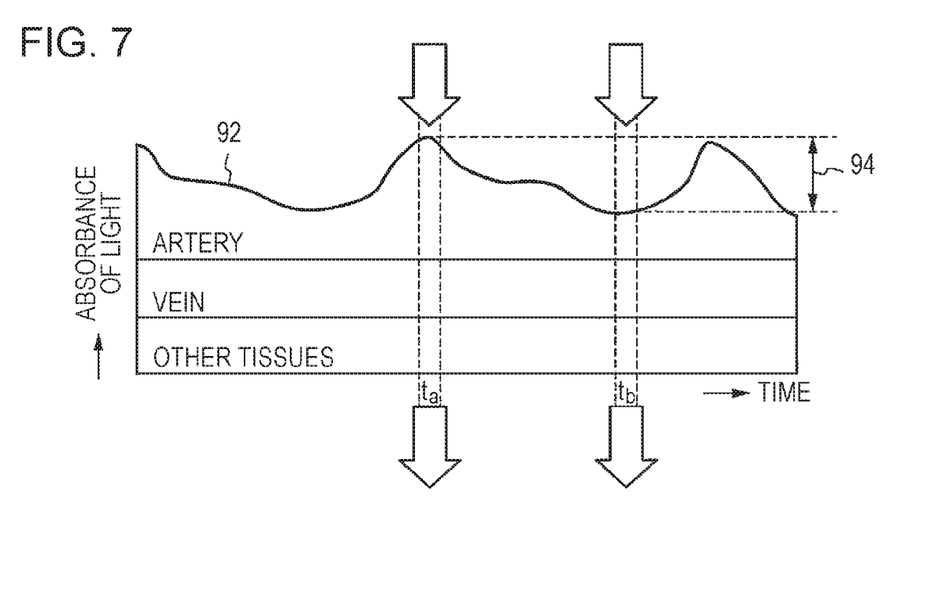
FIG. 7 is a graph illustrating one example of a change in absorbance of light absorbed in a living body.

FIG. 7 is a conceptual diagram illustrating change in absorbance of light that is absorbed, for example, by the living body 8. As illustrated in FIG. 7, the amount of light absorbed by the living body 8 tends to vary over time.

To be specific, absorbance of light absorbed by the living body 8 occurs mainly due to change in absorbance of light absorbed by the artery 4. Change in absorbance of light absorbed by other organs, such as the vein 5 and stationary tissues, are negligible compared with the change that occurs due to the artery 4. This is because arterial blood, which is pumped out of the heart, moves in the artery 4 with pulses to cause the artery 4 to expand and contract with time in the direction along a cross-section the artery 4, and thereby the thickness of the artery 4 changes. A range shown by an arrow 94 in FIG. 7 shows a variation of amount of light absorbance by received light that occurs in accordance with the variation in the thickness of the artery 4.

Referring to FIG. 7, the variation ΔA in the amount of light absorbed due to the change in the thickness of the artery 4 is represented by the following expression (1), where $I_a$ is the amount of light received at a time $t_a$, and $I_b$ is the amount of light received at a time $t_b$.

$$\Delta A = \ln(I_b/I_a) \quad (1)$$

It is known that hemoglobin to which oxygen is bound (oxidized hemoglobin), flowing through the artery 4, tends to absorb light having a frequency of, in particular, about 880 nm in an infrared range, and hemoglobin to which oxygen is not bound (reduced hemoglobin) tends to absorb light having a frequency of, in particular, about 665 nm in a red-color range. Moreover, it is known that oxygen saturation is proportional to the ratio of the variations ΔA in the amounts of absorbed light for different wavelengths.

Accordingly, a combination of infrared light (IR light) and red light, between which the amounts of light absorbed by oxidized hemoglobin and reduced hemoglobin differ more significantly than other combinations, is used. Then, the oxygen saturation S is calculated by using expression (2), where $\Delta A_{IR}$ is a variation of IR light absorbed by the living body 8, $\Delta A_{Red}$ is a variation of red light absorbed by the living body 8, and k is the proportional constant.

$$S = k(\Delta A_{Red}/\Delta A_{IR}) \quad (2)$$

That is, when calculating blood oxygen saturation, plural light-emitting elements 1 that emit light beams having different wavelengths, to be specific, a light-emitting element 1A that emits an IR light beam and a light-emitting element 1B that emits a red light are caused to emit light beams so that the light-emission periods do not overlap. Reflected or transmitted light beams emitted from the light-emitting elements 1A and 1B and reflected or transmitted by the living body 8 are received by using the light-receiving element 3. Then, the oxygen saturation is measured by calculating the values of expression (1) and expression (2) (or other expressions obtained by transforming these expressions) by using the amounts of light received at light-receiving times.

For example, the variation ΔA in the amount of absorbed light may be represented by the following expression (3), which is obtained by transforming expression (1).

$$\Delta A = \ln I_b - \ln I_a \quad (3)$$

Expression (1) is also transformed into the following expression (4).

$$\Delta A = \ln(I_b/I_a) = \ln(1 + (I_b - I_1)) \quad (4)$$

Since usually $(I_b - I_1) \ll I_a$, $\ln(I_b/I_a) \approx (I_b - I_a)/I_a$. Therefore, instead of expression (1), the following expression (5) may be used to represent the variation ΔA in the amount of absorbed light.

$$\Delta A \approx (I_b - I_a)/I_a \quad (5)$$

Hereinafter, the light-emitting element 1A, which emits an IR light beam, will be referred to as a "light-emitting element LD2"; and the light-emitting element 1B, which emits a red light, will be referred to as a "light-emitting element LD3". In the present exemplary embodiment, multi-mode lasers, which generate a larger amount of light, are used as the light-emitting elements LD2 and LD3, because a large amount of light is necessary in order to increase the S/N ratio.

That is, in the present exemplary embodiment, a single-mode laser is used as the light-emitting element LD1 for measuring blood flow information, and multi-mode lasers are used as the light-emitting elements LD2 and LD3 for measuring blood oxygen saturation.

Figure 8:
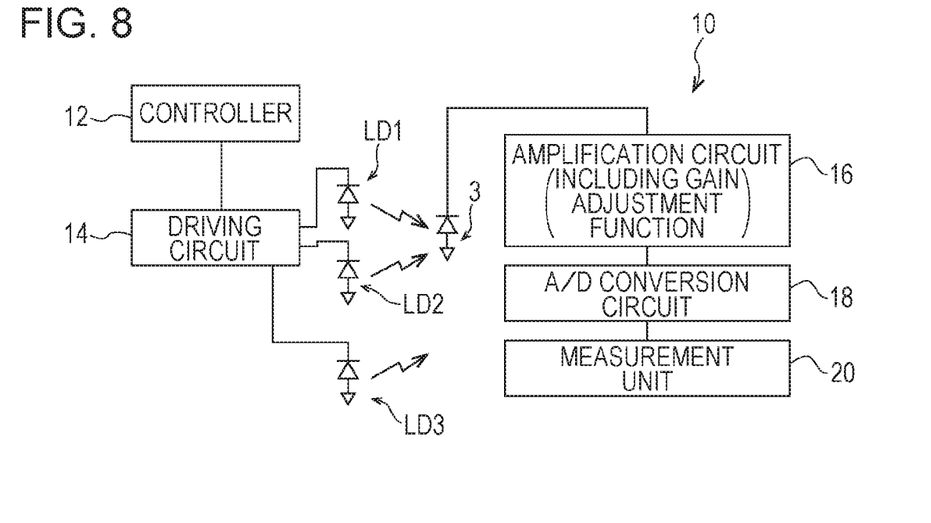
FIG. 8 is an exemplary block diagram of the living-body information measuring device.

FIG. 8 is an exemplary block diagram of a living-body information measuring device 10 according to the present exemplary embodiment.

As illustrated in FIG. 8, the living-body information measuring device 10 includes a controller 12, a driving circuit 14, an amplification circuit 16, an analog/digital (A/D) conversion circuit 18, a measurement unit 20, the light-emitting elements LD1 to LD3, and the light-receiving element 3.

The driving circuit 14 includes a power supply circuit that supplies electric power to the light-emitting elements LD1 to LD3. To the driving circuit 14, the controller 12 outputs a control signal for controlling the light-emission cycles and the light-emission periods of the light-emitting elements LD1 to LD3.

When receiving the control signal from the controller 12, the driving circuit 14 supplies electric power to the light-emitting elements LD1 to LD3 to drive the light-emitting elements LD1 to LD3 in accordance with the light-emission cycles and the light-emission periods indicated by the control signal.

The amplification circuit 16 amplifies a voltage, which corresponds to the intensity of light received by the light-receiving element 3. Here, for example, the light-receiving element 3 outputs a voltage corresponding to the intensity of received light. Alternatively, the light-receiving element 3 may output an electric current corresponding to the intensity of received light. In this case, the amplification circuit 16 amplifies the electric current output from the light-receiving element 3.

The amplification circuit 16 has a gain adjustment function and performs gain adjustment so that the level of a signal amplified by the amplification circuit 16 falls within a specified input range of the A/D conversion circuit 18.

The voltage amplified by the amplification circuit 16 is input to the A/D conversion circuit 18. The A/D conversion circuit 18 digitizes the amount of light received by the light-receiving element 3, which is represented by the voltage, and outputs the digitized amount of light absorbed.

The amount of light absorbed, which has been digitized by the A/D conversion circuit 18, is input to the measurement unit 20. The measurement unit 20 performs FFT on the amount of light emitted from the light-emitting element LD1 and received by the light-receiving element 3 to calculate the spectrum distribution for the frequency ω. Then, the measurement unit 20 measures blood flow information by using the spectrum distribution and the frequency ω.

The amount of light absorbed, which has been digitized by the A/D conversion circuit 18, is input to the measurement unit 20. The measurement unit 20 manages time-series data of the amount of light emitted from the light-emitting element LD2 and the light-emitting element LD3 and received by the light-receiving element 3. The measurement unit 20 measures the oxygen saturation by calculating the variation $\Delta A_{IR}$ in the amount of light emitted from the light-emitting element LD2 and absorbed by the living body 8 and the variation $\Delta A_{Red}$ in the amount of light emitted from the light-emitting element LD3 and absorbed by the living body 8 by using expression (1), and by calculating the ratio of the variation $\Delta A_{Red}$ in the amount of absorbed light to the variation $\Delta A_{IR}$ in the amount of absorbed light by using expression (2).

Figure 9:
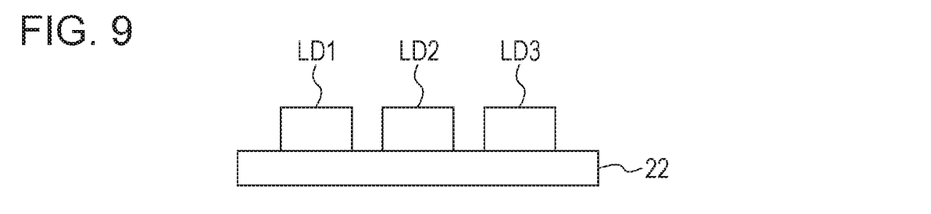
FIG. 9 illustrates an example of an arrangement of light-emitting elements.

As illustrated in FIG. 9, the light-emitting elements LD1 to LD3 are formed on the same semiconductor substrate 22. Thus, reduction in the size of the device is realized. In the present exemplary embodiment, surface-emitting lasers are used as the light-emitting elements LD1 to LD3. Alternatively, edge-emitting lasers may be used.

As described above, when the measurement unit 20 measures the blood flow information, the spectrum distribution of light-receiving amount due to a beat signal is used. Therefore, preferably, laser devices that are capable of easily generating a beat signal is used as the light-emitting element LD1.

However, it is not necessary that light used to measure oxygen saturation be a laser beam, as long as it is possible to calculate the variations $\Delta A_{IR}$ and $\Delta A_{Red}$ in amount of absorbed light. Therefore, light-emitting diodes (LEDs) or organic light-emitting diodes (OLEDs), each of which emits an LED light beam, may be used as the light-emitting elements LD2 and LD3. Accordingly, the combination of the light-emitting elements LD2 and LD3 may be any one of a combination of multi-mode lasers, a combination of light emitting diodes, and a combination of a multi-mode laser and a light emitting diode.

Thus, because a single-mode laser is used to measure blood flow information and two multi-mode lasers are used to measure oxygen saturation, it is possible to measure the blood flow information and the oxygen saturation with high precision, compared with a case where measurement is performed by using only a single-mode laser beam.

Next, the light-emission pattern of the light-emitting elements LD1 to LD3 will be described.

Figure 10:
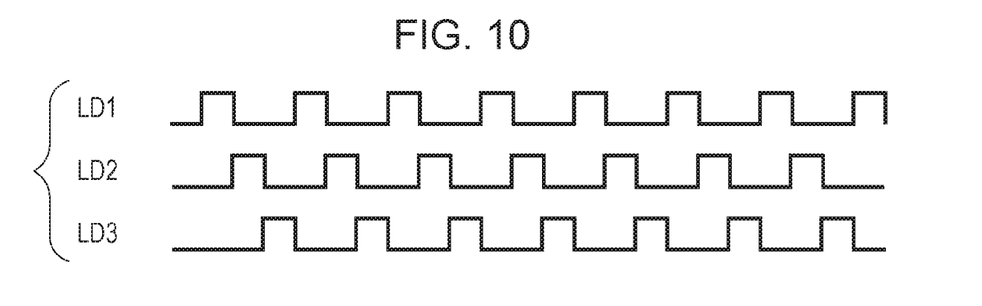
FIG. 10 illustrates one example of a light-emission pattern.

FIG. 10 illustrates an example of the light-emission pattern. In the light-emission pattern illustrated FIG. 10, the light-emitting elements LD1 to LD3 are controlled to emit light beams successively. In the light-emission pattern illustrated in FIG. 10, the lengths of light-emission periods of the light-emitting elements LD1 to LD3 are, for example, the same.

When measuring the blood flow information, because the frequency difference $\Delta\omega_0$ of a beat signal observed by the light-receiving element 3 is within a range of several tens of kilohertz, it is necessary to cause the light-emitting element LD1 to emit laser beams with a frequency that is higher than or equal to twice the frequency difference $\Delta\omega_0$. In contrast, when measuring the blood oxygen saturation, it is sufficient that the frequency of measuring the amounts of received light be in the range of from about 30 to 1000 Hz. Therefore, it is sufficient that the frequency of the light-emission timings of light-emitting elements LD2 and LD3 be in the range of from about 30 to 1000 Hz. That is, it is not necessary to cause the light-emitting elements LD2 and LD3 to emit light beams in synchronism with the frequency of the light-emission timings of the light-emitting element LD1. The frequency of the light-emission timings of the light-emitting elements LD2 and LD3 may be lower than that of the light-emitting element LD1.

Figure 11:
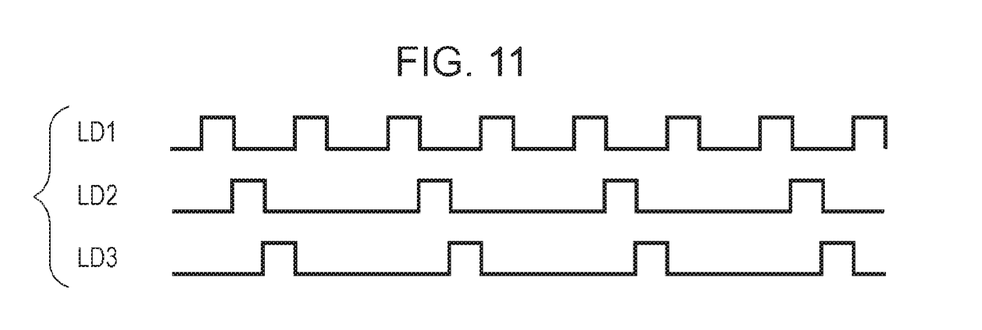
FIG. 11 illustrates one example of a light-emission pattern.

Accordingly, as in the light-emission pattern illustrated in FIG. 11, the frequency of the light-emission timings of the light-emitting elements LD2 and LD3 may be lower than that of the light-emitting element LD1. That is, the number of times the light-emitting elements LD2 and LD3 emit light beams per unit time may be smaller than that of the light-emitting element LD1.

Figure 12:
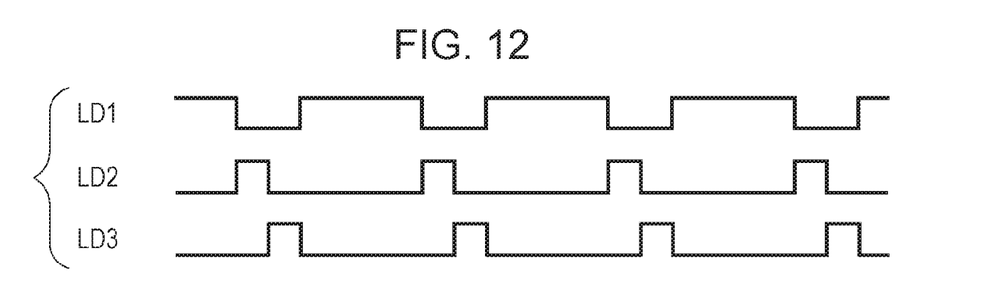
FIG. 12 illustrates one example of a light-emission pattern.

As in the light-emission pattern illustrated in FIG. 12, the light-emitting element LD1 may continuously emit a light beam during each of periods in which the light-emitting elements LD2 and LD3 stop emitting light beams.

When measuring a plethysmogram instead of the oxygen saturation, the light-emitting element LD3 may be omitted. The plethysmogram is measured as follows. For example, the pulse waveform and the pulse rate are measured by using the amount of light emitted from the light-emitting element LD2 and received by the light-receiving element 3, because the amount of light received by the light-receiving element 3 changes due to pulsation of an artery. The plethysmogram is obtained by, for example, calculating the second derivative of the pulse waveform. The plethysmogram is used, for example, to estimate a vascular age or to diagnose arteriosclerosis.

Figure 13:
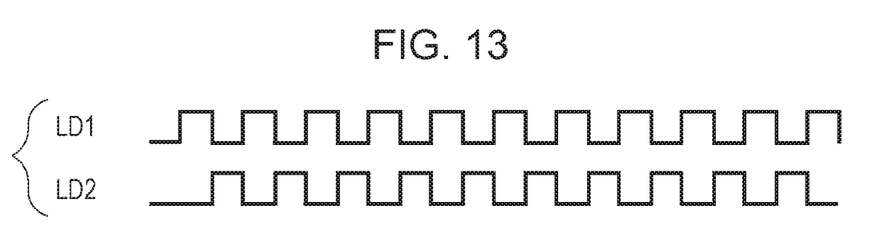
FIG. 13 illustrates one example of a light-emission pattern.

FIG. 13 illustrates an example of light-emission pattern that is used when measuring the blood flow information and the plethysmogram. In the light-emission pattern illustrated in FIG. 13, the light-emitting elements LD1 and LD2 are controlled so as to successively emit light beams. In the light-emission pattern illustrated in FIG. 13, the lengths of the light-emission periods of the light-emitting elements LD1 and LD2 are the same.

As in the case of measuring the oxygen saturation, it is not necessary to cause the light-emitting element LD2 to emit light beams in synchronism with the frequency of the light-emission timings of the light-emitting element LD1. The frequency of the light-emission timings of the light-emitting element LD2 may be lower than that of the light-emitting element LD1.

Figure 14:
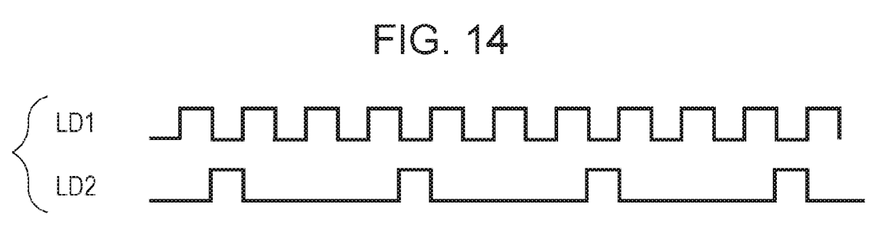
FIG. 14 illustrates one example of a light-emission pattern.

Accordingly, as in the light-emission pattern illustrated in FIG. 14, the frequency of the light-emission timings of the light-emitting element LD2 may be lower than that of the light-emitting element LD1. That is, the number of times the light-emitting element LD2 emit light beams per unit time may be smaller than that of the light-emitting element LD1.

Figure 15:
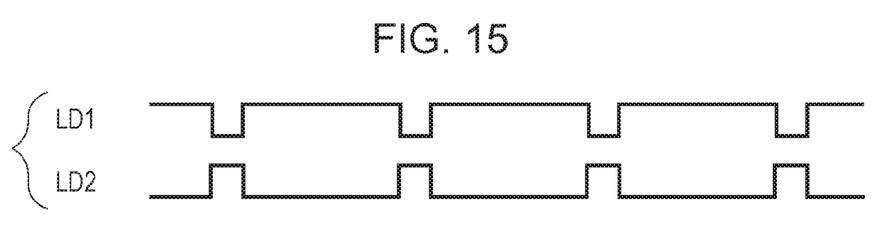
FIG. 15 illustrates one example of a light-emission pattern.

As in the light-emission pattern illustrated in FIG. 15, the light-emitting element LD1 may continuously emit a light beam during each of periods in which the light-emitting element LD2 stops emitting a light beam.

In the exemplary embodiment described above, the living-body information measuring device 10 is used to measure the blood flow information, the oxygen saturation, and the plethysmogram. However, the living-body information measuring device 10 may be used to measure a blood component (blood sugar level or the like), the blood pressure, and the like.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:
1. A living-body information measuring device comprising:
a first light-emitting unit configured to emit a single-mode laser beam;
a second light-emitting unit configured to emit multi-mode laser beams;
a light-receiving element configured to receive reflected or transmitted light beams reflected or transmitted by a living body when the first light-emitting unit and the second light-emitting unit emit the beams toward the living body;

a control unit configured to control light-emission periods of the first light-emitting unit and the second light-emitting unit; and a measurement unit configured to measure a plurality of types of living-body information about the living body by using each of the reflected or transmitted light beams that are successively received by the light-receiving element, wherein the second light-emitting unit includes two light-emitting elements configured to emit light beams having different wavelengths, wherein the measurement unit is further configured to measure blood flow information by using the single-mode laser beam and oxygen saturation of the living body by using the multi-mode lasers, wherein, in a case that the measurement unit measures the blood flow as a first one of the plurality of types of living body information, the control unit controls the first light-emitting unit to emit the single mode laser beam at a first frequency greater than or equal to twice of a frequency difference of a beat signal measured by the measurement unit, wherein, in a case that the measurement unit measures the oxygen saturation as a second one of the plurality of types of living body information, the control unit controls the second light-emitting unit to emit the multi-mode light beam at a second frequency, and wherein the second frequency is lower than the first frequency.

2. The living-body information measuring device according to claim 1,
wherein the control unit is further configured to control the light-emission periods so that the first light-emission period of the first light-emitting unit and the second light-emission period of the second light-emitting unit do not overlap.

3. The living-body information measuring device according to claim 1,
wherein the measurement unit is further configured to measure blood flow information and a plethysmogram of the living body as the living-body information.

4. The living-body information measuring device according to claim 1, further comprising:
a gain-adjusting unit configured to perform gain adjustment so that a level of a light-receiving signal that corresponds to each of the light beams received by the light-receiving element falls within a specified range.

5. The living-body information measuring device according to claim 1,
wherein the first light-emitting unit and the second light-emitting unit are formed on a same semiconductor substrate.

6. The living-body information measuring device according to claim 1,
wherein the first light-emitting unit is a first surface-emitting laser, and
wherein the second light-emitting unit is further configured to emit the multi-mode light beam and is a second surface-emitting laser.

7. The living body information measuring device according to claim 1,
wherein the first frequency is greater than 20 kilohertz, and
wherein the second frequency is among a range of 30 to 1000 hertz.

8. The living body information measuring device according to claim 1, further comprising a third light-emitting unit configured to emit a light beam,
wherein the control unit is further configured to control a third light-emission period of the third light-emitting unit such that the third light-emission period begins as the second light-emission period ends and a fourth light emission period of the first light-emitting unit begins.

9. The living body information measuring device according to claim 1,
wherein, of the light-emission periods, a first light-emission period of the first light-emitting unit ends at a same time as a second light-emission period of the second light-emitting unit begins.

10. A light-emitting apparatus comprising:
a first light-emitting unit configured to emit a single-mode laser beam;
a second light-emitting unit configured to emit a multi-mode light beam or an LED light beam,
a control unit configured to control light emission periods of the first light-emitting unit and second light emitting unit,
wherein the first light-emitting unit and the second light-emitting unit are formed on a same semiconductor substrate, and
wherein, of the light-emission periods of the first light emitting unit and the second light-emitting unit, a first light-emission period of the first light-emitting unit ends at a same time as a second light-emission period of the second light-emitting unit begins.

11. The light-emitting apparatus according to claim 10,
wherein the first light-emitting unit is a first surface-emitting laser, and
wherein the second light-emitting unit is further configured to emit the multi-mode light beam and is a second surface-emitting laser.

* * * * *